United States Patent [19]

Latorre

[11] Patent Number: 4,850,067

[45] Date of Patent: Jul. 25, 1989

[54] ORTHOPEDIC PILLOW WHICH MINIMIZES SNORING

[76] Inventor: Nestor R. Latorre, 7A Playamar Condominiums, Isla Verde, P.R. 00913

[21] Appl. No.: 110,433

[22] Filed: Oct. 20, 1987

Related U.S. Application Data

[63] Continuation-in-part of Ser. No. 854,796, Apr. 23, 1986, abandoned.

[51] Int. Cl.$^4$ .............................................. A47C 20/00
[52] U.S. Cl. ......................................... 5/431; 5/436; 5/441; 5/437
[58] Field of Search ................... 5/431, 432, 434–437, 5/440–442

[56] References Cited

U.S. PATENT DOCUMENTS

| | | | |
|---|---|---|---|
| 2,940,088 | 6/1960 | Boos | 5/436 |
| 3,243,828 | 4/1966 | McCarty | 5/437 |
| 3,480,976 | 12/1969 | Yavner | 5/436 |
| 3,482,571 | 12/1969 | Behrendt | 5/436 X |
| 4,218,792 | 8/1980 | Kogan | 5/436 |

FOREIGN PATENT DOCUMENTS 1941603 3/1978 Fed. Rep. of Germany .......... 5/435

Primary Examiner—Gary L. Smith
Assistant Examiner—Michael F. Trettel
Attorney, Agent, or Firm—Dressler, Goldsmith, Shore, Sutker & Milnamow, Ltd.

[57] ABSTRACT

An orthopedic pillow which enhances muscular relaxation during sleep and which minimizes snoring is constituted by a soft compressible material which underlies the head, nape of the neck and shoulders of a sleeper lying on his back. This pillow is generally rectangular in plan view and has its upper surface contoured to provide laterally spaced upstanding side margins at each side of a body-supporting central region. The central region has a centrally positioned nape-supporting portion of greatest elevation convexly curved from top to bottom and concavely curved from side to side to support the nape of the neck. The nape-supporting portion separates: (1) a side to side concave portion at the upper end of said pillow which is inclined downwardly from its highest point at said nape-supporting portion to a low point at the occipital portion of the head for supporting the back of the head; from (2) a second portion at the lower end of said pillow for supporting the upper portion of the back which is inclined downwardly from its highest point at said nape-supporting portion to a lower end of minimum elevation. The back-supporting inclined portion is bordered at both sides thereof by shoulder-receiving depressions where the pillow is of minimum thickness.

9 Claims, 1 Drawing Sheet

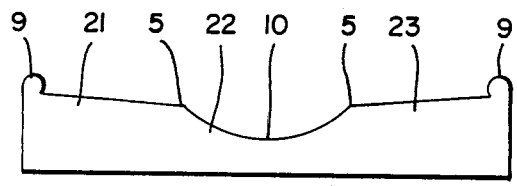
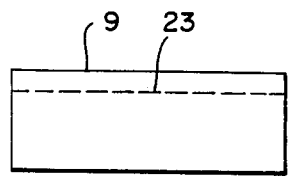
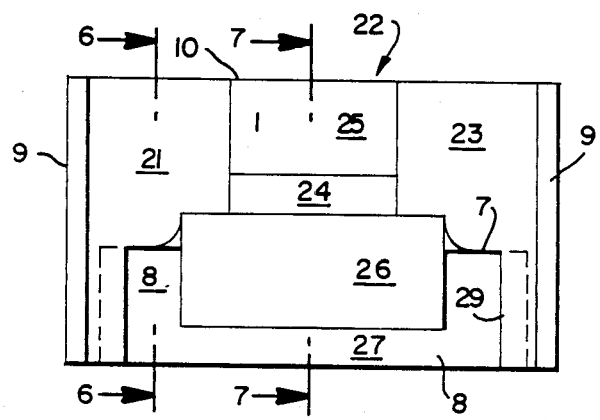
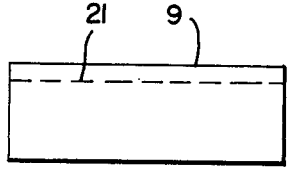
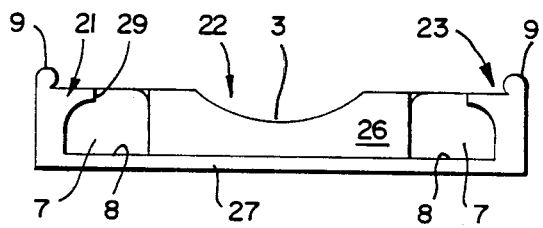
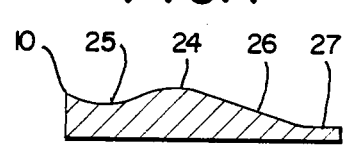
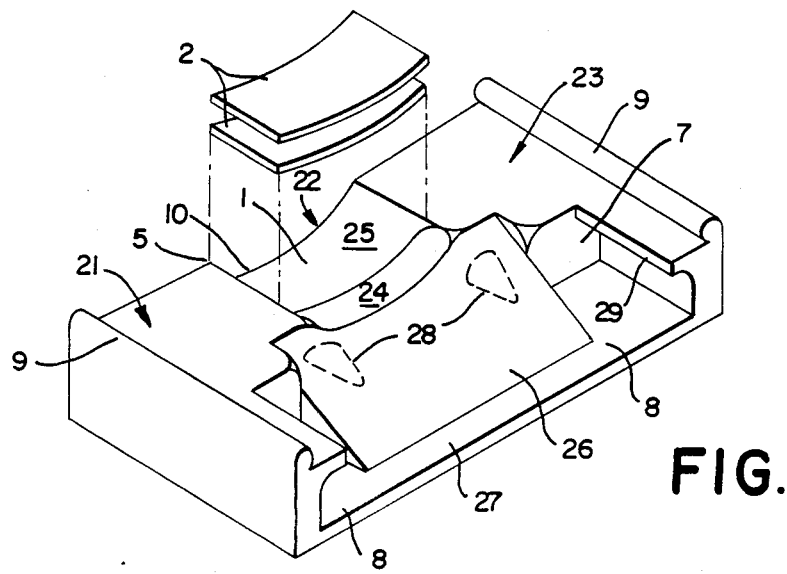

ORTHOPEDIC PILLOW WHICH MINIMIZES SNORING

This application is a continuation-in-part of my prior application Ser. No. 854,796, filed Apr. 23, 1986. abandoned

TECHNICAL FIELD

This invention relates to orthopedic pillows which enhance muscular relaxation during sleep and which minimize snoring.

BACKGROUND ART

Snoring is an involuntary sound produced mostly by men during sleep, men being prone to snore more frequently than women by a 95 to 5 ratio.

During sleep, the muscle tone falls, the neck bends forward, and the tongue goes up and back, creating the basic cause of snoring: an obstruction of the throat and the respiratory air pathway. The relaxed pharyngeal membranes surrounding muscles, and the top of the tongue, stand in the way of the air, while the sleeper makes quite an effort to succeed in the inhaling process. Air strikes these obstacles trying to pass them, producing the sound of the snore.

For example: if we bend or adhere objects within the lumen of a pipe, and air passes through this obstructed passage, a sound is produced which resembles a policeman's whistle. Our nostrils, pharynx, trachea and bronchi are built like pipes. If the neck is bent, if membranes or mucous linings are irritated, or if there are polyps present, or if there is chronic tonsilitis or adenoid hypertrophy, the free air pathway will be clogged and the noise will be directly proportional to the grade of pharyngeal obstruction.

Familiar symptoms of snoring are observed when one awakens in the morning to experience a dry throat and a feeling of tiredness due to the effort of breathing which causes sleep to be superficial and to produce little real rest. When snoring is repeated night after night, the snorer becomes weary, impatient, irritable and tends to feel a sadness which can develop into a symptomatic depression. In the long run, the snorer can lose interest in sex, encounter erection difficulties and ultimately develop impotence, all without apparent reason.

A forceful inhalation process during sleep lasting up to 10 seconds is called an APNEA. This syndrome is characterized by a potentially lethal condition which results from multiple and repetitive obstructions in breathing during sleep. When a loud choking gasp is heard, it is because the sleeper succeeded in overcoming the occlusion. When this syndrome lasts more than 10 seconds, sinus arrest and sudden death can develop due to arrythmia or hypoxia. This syndrome can also develop into premature ventricular contractions, ventricular tachycardias towards an atrioventricular block, and ultimately cardiac failure. In all of the instances mentioned above, and f physical trauma is present, and if the neck bends forwardly or laterally while snoring, the pain will increase, sleep relaxation will decrease, and the healing time will be extended. The correct physiologic position will minimize pain and shorten the regenerative physical process.

It is the objective of this invention to provide a pillow which will help maintain the head and nostrils in a straight position for better ventilation and reduced diaphragmatic effort. In this way, the tendency to snore will be minimized and the complications of snoring will be reduced.

Also, the sleeper's head is frequently not in a very relaxed position, and this imposes stresses and strains upon the neck and upper portions of the back leading to considerable discomfort the following day. When these stresses and strains persist, they can lead to all sorts of physical breakdowns.

Previous orthopedic pillows have addressed only the isolation of the head and neck, following the basic patterns of ordinary pillows which leave the shoulders free of proper support. The counterweight of the head is thus sustained entirely on the cervix, producing cervical musculature strain and tracheal obstruction. Resting on a fixed joint after an injury can cause lack of muscular relaxation and comfort, thus delaying the healing process. Consequently, the prior cervical pillows can produce neck muscular strain and the local pharyngeal musculature can contract and obstruct the respiratory pathways which can cause snoring to increase.

The configured pillow of this invention not only helps to maintain an open passageway to ease the burden of breathing and minimize the tendency to snore, thus reducing the noise level which is so objectionable to others, but it also minimizes the described ailments and discomforts and helps to regenerate damaged tissue.

DISCLOSURE OF INVENTION

In accordance with this invention, an orthopedic pillow is provided which enhances muscular relaxation during sleep and which minimizes snoring. This pillow comprises a soft compressible material which underlies the head, nape of the neck and shoulders of a sleeper lying on his back and is generally rectangular in plan view with its upper surface contoured to provide laterally spaced upstanding side margins at each side of a body-supporting central region. The preferred compressible materials are foam or sponge rubbers which may be used alone or in conjunction with inflatable inserts.

The upstanding side margins reduce the tendency of the sleeper to roll over, and when the sleeper has turned on his side, they elevate and support the side of the face. The central region has a centrally positioned nape-supporting portion of greatest elevation which is convexly curved from top to bottom and concavely curved from side to side to support the nape of the neck. This nape-supporting portion separates: (1) a side to side concave portion at the upper end of the pillow which is inclined downwardly from its highest point at the nape-supporting portion to a low point at the occipital portion of the head for supporting the back of the head; from (2) a second portion at the lower end of the pillow for supporting the upper portion of the back which is inclined downwardly from its highest point at said nape-supporting portion to a lower end of minimum elevation.

The angles of downward inclinations of the portions (1) and (2) are preferably at an angle of 10°–15°.

The back-supporting inclined portion is bordered at both sides thereof by shoulder-receiving depressions of minimum thickness which are preferably each formed with a step at their upper end. This step separates the shoulder-receiving depressions from the upper portion of one of the upstanding side margins which is adapted to support the side of the face when the sleeper rolls to one side. More particularly, these upstanding side margins are sloped downwardly from the sides in and from the nape-supporting portion to the top of the pillow.

Referring more particularly to the accompanying drawings:

FIG. 1 is a rear elevation of a pillow constructed in accordance with this invention;

FIG. 2 is a top plan view of the pillow of FIG. 1;

FIG. 3 is a front elevation of the pillow of FIG. 1;

FIG. 4 is a right side view of the pillow of FIG. 1;

FIG. 5 is a left side view of the pillow of FIG. 1;

FIG. 6 is a cross-section taken on the line 6—6 of FIG. 2;

FIG. 7 is a cross-section taken on the line 7—7 of FIG. 2; and

FIG. 8 is a plan view of the pillow of FIG. 1 with optional pads which can be used to adjust the position of the head during sleep.

Referring more particularly to the drawings, an illustrative pillow is shown without any casing, albeit one can use a conventional pillow slip or a configured one to cover the pillow which is shown. The pillow is made of soft compressible load bearing material, such as sponge rubber. While the pillow shown is simple a block of sponge rubber cut to shape, any resilient soft material can be molded to shape, or the substance of the pillow can be allowed to foam into a mold of appropriate shape.

One can also leave the interior of the pillow open and seal it with a valve or employ an inflatable insert to allow the configured pillow to be inflated or filled with a liquid to a comfortable load bearing condition for use. All of these variations are within the scope of this invention in which it will be understood that it is the configuration of the pillow which is important.

The pillow of this invention is intended to underlie the head, nape of the neck and shoulders of a sleeper lying on his back, and is sized for that purpose. The pillow is generally rectangular in plan view, as shown in FIGS. 2 and 8 and is formed with a flat bottom.

This soft and resilient pillow is formed with three regions each of which extends from the top of the pillow to the bottom of the pillow. These regions which can be seen in FIG. 1. where they are identified by numerals 21, 22, and 23. More particularly, the pillow's upper surface is contoured to provide laterally spaced upstanding side margins 21 and 23 (which support the face when the sleeper rolls onto his side) at each side of a body-supporting central region 22 (only the support for the top of the head can be seen in FIG. 1).

This central region 22 is more easily seen in FIGS. 2 and 8 where it can be seen to have a centrally positioned nape-supporting portion 24 of greatest elevation. This nape-supporting portion in FIGS. 3 and 8 can be seen to be concavely curved from side to side to support the nape of the neck. As will be seen in FIGS. 7 and 8, the nape-supporting portion 24 is convexly curved from top to bottom to spread the weight of the neck and thus provide a comfortable support therefor.

The sides of the upstanding side margins 21 and 23 terminate in raised ribs 9 which may be of any desired cross-sectional configuration. These ribs 9 help to limit the rolling motion of the sleeper, albeit they can be omitted. These ribs are shown in dotted lines in FIGS. 4 and 5.

FIGS. 2, 7 and 8 further show that the central region of the pillow has a centrally positioned nape-supporting portion of greatest elevation (in that region) which separates a side to side and top to bottom concave portion 25 at the upper end of the pillow from a second portion 26 at the lower end of the pillow. The portion 25 at the upper end of the pillow is inclined downwardly from its highest point at the nape-supporting portion to a low point 1 for supporting the back of the head at the occipital area thereof. The second portion 26 at the lower end of the pillow supports the upper portion of the back, and this second portion is inclined downwardly from its highest point at the nape-supporting portion to a lower end of minimum elevation where it joins the base of the pillow 27.

It will also be seen that the back-supporting inclined portion 26 is bordered at both sides by shoulder-receiving depressions 8 of minimum thickness (the thickness of the base 27). This allows the sleeper to roll to either side while the weight of his shoulder holds the pillow in place. While the sleeper is on his side, his face rests on one of the upstanding side margins 21 and 23.

It has previously been pointed out that the each of the two portions in the central region which join the nape-supporting portion are downwardly inclined. The angles of these downward inclinations are preferably at an angle of 10°-15°.

Referring more particularly to the shoulder-receiving depressions 8, each of these is formed with a step 7 at its upper end. This step separates the shoulder-receiving depression from one of the upstanding side margins 21 and 23 which are intended to support the side of the face when the sleeper rolls to one side, as previously noted. The step 7 places the adjoining upstanding side margin into an appropriately elevated position to receive the side of the face.

Moreover, and to properly configure the upstanding side margins, these are preferably sloped downwardly from the sides in and from the nape-supporting portion to the top of the pillow. The angle of slope in each direction is preferably about 8°.

Back-supporting portion 26, as seen in FIG. 8, preferably includes scappula-receiving areas 28 formed by cutting out the areas indicated by dotted lines and replacing them with correspondingly-shaped pieces of greater hardness and firmness to better support the scappula. In addition, optional pads 2 may be placed in occipital-receiving portion 1 of the pillow (in the manner of a shim) to adjust that portion to the proper height for the individual sleeper, and similar pads, not shown, can be used to elevate the nape-supporting portion 24.

It will also be seen that portion 25 of the pillow terminates at its upper end in an elevated portion 10 which help to support the back of the head near the top thereof.

Also, adjacent the shoulder-receiving depressions 8, the upstanding portions 21 and 23 are formed at their upper surface with inwardly extending ledges 29. The ledges 29 help to limit the rolling motion of the sleeper.

To illustrate suitable proportions for the pillow of this invention, the pillow has an extreme height of four inches, and the upstanding side portions have a length (across the upper end of the pillow) of six inches. At the occipital portion 10, the pillow has a height of two inches and is three and one quarter inches high at point 5.

The shoulder-receiving spaces are each four and one half inches by six inches large, and the ledges 29 cut down the length of the step 7 to 3 inches at the top. The width of the upstanding portion at the lower end of the pillow is one and one half inches and are four inches high.

The shoulder-receiving portion 26 is fourteen inches in length and extends for six inches toward the lower end of the pillow where the base 27 extends for an additional two inches.

The nape-receiving portion is two and one half inches high at its lowest point, two inches in width and extends across the length of the pillow for nine inches. The pads 2 are selected by the sleeper for best fit and are one quarter inch thick. These pads may be adhesively secured to the portion 25.

The ridges 9 are one inch high and one inch thick and extend along the entire side of the pillow for a distance of fourteen and one half inches.

The face-receiving surfaces provided by the upstanding portions 21 and 23 are eight and a half inches long and six inches wide, and the steps 7 are three and one half inches high.

What is claimed is:

1. An orthopedic pillow which enhances muscular relaxation during sleep and which minimizes snoring comprising, a soft compressible material which underlies the head, nape of the neck and shoulders of a sleeper lying on his back, said pillow being generally rectangular in plan view to define a top, a bottom and opposite sides, and having an upper surface contoured to provide laterally spaced upstanding side margins at each side of a body-supporting central region, said central region having a centrally positioned nape-supporting portion of greatest elevation convexly curved from top to bottom and concavely curved from side to side to support the nape of the neck, said nape-supporting portion separating: (1) a side to side concave portion at the
    top end of said pillow, said side to side concave portion having a highest portion
    at said nape-supporting portion and being inclined downwardly from said highest portion to a low point at the occipital portion of the head for supporting the back of the head; from (2) a second portion at the bottom of said pillow for supporting the upper portion of the back, said second portion being inclined downwardly from said nape-supporting portion to a lower end at the bottom of said of said pillow , said back-supporting inclined portion being bordered at opposite sides thereof by shoulder-receiving depressions
    set into the pillow and forming a base portion
    of minimum thickness
    that surrounds said base portion.

2. An orthopedic pillow as recited in claim 1 in which the angles of downward inclinations of said portions (1) and (2) are at an angle of 10°-15°.

3. An orthopedic pillow as recited in claim 1 in which said shoulder-receiving depressions are each formed with a step at an upper end, said step separating said shoulder-receiving depressions from the upper surface of one of said upstanding side margins which is adapted to support the side of the face when said sleeper rolls to one side.

4. An orthopedic pillow as recited in claim 3 in which said upstanding side margins are sloped downwardly from the sides of said pillow in and from said nape-supporting portion to the top of said pillow.

5. An orthopedic pillow as recited in claim 4 in which said upstanding side margins are sloped in each of said directions at an angle of about 8°.

6. An orthopedic pillow as recited in claim 1 in which said second portion includes scapula receiving portions of greater hardness and firmness to better support the scappula.

7. An orthopedic pillow as recited in claim 1 in which said pillow is made of a foam or sponge rubber.

8. An orthopedic pillow as recited in claim 1 in which said upstanding side margins terminate at the sides of said pillow in raised ribs to help limit the rolling motion of the sleeper.

9. An orthopedic pillow as recited in claim 1 in which said upstanding portions adjacent said shoulder-receiving depressions are bordered at the sides of said pillow by a portion of said upstanding side margins which terminate in inwardly extending ledges to help limit the rolling motion of the sleeper.

* * * * *